(12) United States Patent
Guan et al.

(10) Patent No.: US 12,618,107 B2
(45) Date of Patent: *May 5, 2026

(54) METHODS FOR FORMING ADAPTER LIGATED NUCLEIC ACID MOLECULES

(71) Applicant: New England Biolabs, Inc., Ipswich, MA (US)

(72) Inventors: Shengxi Guan, Stoneham, MA (US); Sean Maguire, Gloucester, MA (US)

(73) Assignee: New England Biolabs, Inc., Ipswich, MA (US)

( * ) Notice: Subject to any disclaimer, the term of this patent is extended or adjusted under 35 U.S.C. 154(b) by 1218 days.

This patent is subject to a terminal disclaimer.

(21) Appl. No.: 17/594,534

(22) PCT Filed: Apr. 24, 2020

(86) PCT No.: PCT/US2020/029761
§ 371 (c)(1),
(2) Date: Oct. 21, 2021

(87) PCT Pub. No.: WO2020/219838
PCT Pub. Date: Oct. 29, 2020

(65) Prior Publication Data
US 2022/0213539 A1 Jul. 7, 2022

Related U.S. Application Data

(63) Continuation of application No. 16/796,113, filed on Feb. 20, 2020, now Pat. No. 11,390,915.
(Continued)

(51) Int. Cl.
*C12Q 1/6855* (2018.01)
*C12N 15/10* (2006.01)

(52) U.S. Cl.
CPC ....... *C12Q 1/6855* (2013.01); *C12N 15/1093* (2013.01); *C12N 15/1096* (2013.01); *C12Q 2525/191* (2013.01)

(58) Field of Classification Search
CPC ............ C12Q 1/6855; C12Q 2525/191; C12Q 2525/179
See application file for complete search history.

(56) References Cited

U.S. PATENT DOCUMENTS 8,163,479 B2 4/2012 Jaccard et al.
8,178,314 B2 5/2012 Kindermann et al.
(Continued)

FOREIGN PATENT DOCUMENTS

WO 2012158603 A2 11/2012
WO WO-2018193233 A1 * 10/2018 ......... C12N 15/1093

OTHER PUBLICATIONS

Sultan et al., "Influence of RNA extraction methods and library selection schemes on RNA-seq data," BMC Genomics, vol. 15, pp. 1-13. (Year: 2014).*
(Continued)

*Primary Examiner* — Young J Kim
(74) *Attorney, Agent, or Firm* — New England Biolabs, Inc

(57) ABSTRACT

Compositions and methods of use are provided that among other things, allow for efficient adapter ligation to small RNAs. Embodiments of the compositions include partially double stranded polynucleotides for use as 3' adapters that contain a cleavable linker positioned between a single-stranded region and a double-stranded region. Upon ligating the 3' adapters, the single-stranded region is released by cleaving the cleavable linker.

16 Claims, 10 Drawing Sheets

Specification includes a Sequence Listing.

Related U.S. Application Data

(60) Provisional application No. 62/839,191, filed on Apr. 26, 2019.

(56) References Cited

U.S. PATENT DOCUMENTS

| | | | |
|---|---|---|---|
| 8,227,602 B2 | 7/2012 | Gautier et al. | |
| 8,975,388 B2 | 3/2015 | Zichi et al. | |
| 11,390,915 B2 * | 7/2022 | Guan | C12N 15/1093 |
| 2013/0261027 A1 | 10/2013 | Li et al. | |
| 2014/0357528 A1 | 12/2014 | Robb et al. | |
| 2016/0265031 A1 | 9/2016 | Liu et al. | |
| 2017/0145500 A1 | 5/2017 | Myers et al. | |
| 2018/0010178 A1 | 1/2018 | Charizanis et al. | |
| 2019/0194649 A1 * | 6/2019 | Raine | C12Q 1/686 |

OTHER PUBLICATIONS

Bottani, et al., Journal of Clinical Medicine, 8, 1661 (2019).
Keam, et al., Life 5, 1638-1651 (2015).
Kumar, et al., BMC Biology, 12, 78 (2014).
Shigematsu, et al., Gene Regulation and Systems Biology, 9, 27-33 (2015).
Maguire, et al, Nucleic Acids Research, 48, 14, e80 (2020).
Wu, et al, BMC Genomics, 19, 1, 1-12, 2018.
Hafner, et al., RNA, 17, 9, 1697-1712, 2011.
Gansauge, et al, Nucleic Acids Research, gkx033, 2017.
Giraldez, et al., Nature Biotechnology, 36, 8, 476-757, 2018.
Xu, et al., Methods in next generation sequencing, 2, 1-10, 2015.
Yau, et al., The FEBS Journal, 285, 19, 3669-3682, 2018.

* cited by examiner

Percentage of miRNA within 2-fold of Expected Value
Illumina     14.7%
Bioo         38.3%
Splint       84.3%

FIG. 9

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(24)
<223> OTHER INFORMATION: 3InvdT

<400> SEQUENCE: 1
agatcggaag agcacacgtc tttt                                        24

<210> SEQ ID NO 2
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(21)
<223> OTHER INFORMATION: n at position 21 is ideoxyU
<220> FEATURE:
<221> NAME/KEY: misc_feature
<222> LOCATION: (22)..(22)
<223> OTHER INFORMATION: n at position 22 is a, or t, or g, or c, where
      25 percent of the DNA molecues in the population have a, 25
      percent have t, 25 percent have g and 25 percent have c.
<220> FEATURE:
<221> NAME/KEY: misc_feature
<222> LOCATION: (23)..(27)
<223> OTHER INFORMATION: n is a, c, g, or t

<400> SEQUENCE: 2
agacgtgtgc tcttccgatc nnnnnnnttt                                  30

<210> SEQ ID NO 3
<211> LENGTH: 26
<212> TYPE: RNA
<213> ORGANISM: Artificial Sequence
<220> FEATURE:
<223> OTHER INFORMATION: Synthetic construct

<400> SEQUENCE: 3
guucagaguu cuacaguccg acgauc                                      26

<210> SEQ ID NO 4
<211> LENGTH: 32
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n at position 1 is a, or t, or g, or c where 25
      percent of the DNA molecues in the population have a, 25 percent
      have t, 25 percent have g and 25 percent have c.
<220> FEATURE:
<221> NAME/KEY: misc_feature
<222> LOCATION: (2)..(6)
<223> OTHER INFORMATION: n is a, c, g, or u

<400> SEQUENCE: 4
nnnnnngauc gucggacugu agaacucuga ac                               32
```

-continued

```
<210> SEQ ID NO 5
<211> LENGTH: 35
<212> TYPE: RNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (1)..(6)
<220> FEATURE:
<221> NAME/KEY: misc_feature
<222> LOCATION: (1)..(1)
<223> OTHER INFORMATION: n at position 1 is a, or t, or g, or c where 25
      percent of the DNA molecues in the population have a, 25 percent
      have t, 25 percent have g and 25 percent have c.
<220> FEATURE:
<221> NAME/KEY: misc_feature
<222> LOCATION: (2)..(6)
<223> OTHER INFORMATION: n is a, c, g, or u
<220> FEATURE:
<221> NAME/KEY: misc_feature
<222> LOCATION: (33)..(35)
<223> OTHER INFORMATION: n is t
<220> FEATURE:
<221> NAME/KEY: misc_feature
<222> LOCATION: (33)..(35)
<223> OTHER INFORMATION: n is 3InvdT

<400> SEQUENCE: 5
nnnnnngauc gucggacugu agaacucuga acnnn                                          35
```

METHODS FOR FORMING ADAPTER LIGATED NUCLEIC ACID MOLECULES

CROSS-REFERENCE

This application is a § 371 application of International Application No. PCT/US2020/29761, filed Apr. 24, 2020, which claims the benefit of US Provisional Application 62/839,191, filed on Apr. 26, 2019, and U.S. application Ser. No. 16/796,113, filed Feb. 20, 2020. These applications are incorporated herein by reference in their entireties.

BACKGROUND

Preferential ligation of adapters to some single-stranded RNAs and not others in an RNA library results in inaccurate profiling of a library composition. In order to reduce bias, adapters having single-strand extensions that act as splints can be utilized. However, such adapters can readily ligate with each other in part because of their excess concentration relative to the target RNA. Adapter dimer formation is particularly problematic when the target RNAs are small because the ligation artifacts such as adapter dimers may not be readily distinguished from target RNAs based on size. As a consequence, standard size separation techniques such as electrophoresis are ineffective. Current methods are thus challenged by low sensitivity and high bias, limiting their ability to capture an accurate representation of the cellular small RNA population. Some classes of small RNAs (sR-NAs) contain a 2'-O-methylation (2'OMe) modification on the ribose moiety of the 3' terminal nucleotide. This modification stabilizes the sRNA and is present in endogenous siRNAs, miRNAs in plants and piRNAs in animals (Ghildi-yal, et al. (2009) Nature Reviews Genetics, 10, 94-108). The 2'OMe modification severely impacts ligation efficiency to single-stranded DNA (ssDNA) adapters, as well as the efficiency of the 3' polyadenylation or polyuridylation required for template-switching approaches (Munafo, et al., (2010) RNA, 16, 2537-2552). Combined with structural and sequence biases, this modification can make sequencing and discovery of 2'OMe modified RNA difficult and bias sequencing libraries against modified sRNA (Dard-Dascot, et. al., (2018) BMC Genomics, 19, 118). sRNAs are important regulators of gene expression and are involved in human development and disease. Next-generation sequencing (NGS) allows for scalable, genome-wide studies of sRNA with the proviso that library preparations derived from sRNA populations are representative of the component RNAs. The ligation efficiency and ligation bias of existing single-stranded adapters varies according to the sequence of the target and the adapter. Different adapter sequences can cause profound changes in library content (Jayaprakash, et al., (2011) Nucleic Acids Research, 39, e141-e141; Baran-Gale, et al., (2015) Frontiers in Genetics, 6, 352 and McLaughlin, et al. (1982) 125, 639-643).

SUMMARY

Provided herein, among other things, is a partially double-stranded polynucleotide molecule having a top strand and a bottom strand that can be used as a 3' adapter and thereby may be referred to as a randomized Splint adapter. This polynucleotide molecule is characterized by a first sequence in the top strand. The bottom strand is characterized by a second sequence which is complementary to the first sequence, and a third sequence that is 3' of the second sequence and includes a sequence of at least 4 degenerate nucleotides; and a site-specific cleavable linker that may be a sequence, nucleotide or bond, where the cleavable linker is at or near the junction between the second and third sequences. An embodiment of the partially double stranded polynucleotide serving as a 3' adapter is illustrated as Adapter 2 in FIG. 1. As shown, the nucleotide at the 5' end of the top strand is base paired with the bottom strand such that the double-stranded polynucleotide molecule has a 3' single-stranded extension (or "overhang") comprising the degenerate nucleotides of the bottom strand. The top strand of the 3' adapter may be ligated to a target polynucleotide via a ligation that is splinted by the bottom strand of the 3' adapter, as illustrated in FIG. 1. In some embodiments, the present 3' adapter may be used in conjunction with a 5' adapter, an example of which is also illustrated as Adapter 1 in FIG. 1. As shown, the 5' adapter may be a partially double-stranded polynucleotide molecule having a top strand and a bottom strand, wherein the top strand comprises a first sequence and the bottom strand comprises: a second sequence which is complementary to the first sequence and a third sequence that is 5' of the second sequence and comprises a sequence of at least 4 degenerate nucleotides. In this adapter, the nucleotide at the 3' end of the top strand is base paired with the bottom strand such that the double-stranded polynucleotide molecule has a 5' single-stranded extension (or "overhang") comprising the degenerate nucleotides of the bottom strand. The top strand of the 5' adapter is ligated to the target polynucleotide via a ligation that is splinted by the bottom strand of the 5' adapter, as illustrated in FIG. 1. As illustrated in FIG. 1, the method may involve cleaving the bottom strand of the 3' polynucleotide adapter at the site-specific cleavable sequence, nucleotide or bond so as to remove the degenerate sequence from the ligation products and leave the second sequence hybridized to the ligation products. Where the target polynucleotide is RNA, the 3' end of the second sequence can then be extended by a reverse transcriptase, thereby copying the target RNA to form a cDNA.

The adapters have improved properties including that they generally do not self-ligate but can ligate efficiently to a target polynucleotide such as a target RNA and show reduced bias in binding substantially all RNAs in an RNA library without preference. This is facilitated by a mixture of enzymes that include a 5' exonuclease and a nicking enzyme and may further include a deadenylase. Advantages of embodiments of these adapter compositions for use with sRNAs have been observed to include: increased amount of targeted sRNAs, derived from cell samples, represented in a library for sequencing, reduced background as adapter-dimer formation is prevented, and an improved representation of RNA with reduced bias in a population derived from a cell sample compared with libraries that use single-strand adapter ligation to sRNAs.

Adapter compositions are described herein that include partially double-stranded polynucleotide molecules that can be either DNA or RNA and can be formed from a single polynucleotide strand such as a hairpin or loop structure. Alternatively, the polynucleotide molecule may be formed from two polynucleotide strands. Embodiments of the partially double-stranded polynucleotide molecules include a top strand and a bottom strand, wherein the top strand is complementary to a portion of the bottom strand to form the double-stranded region. The bottom strand has a non-complementary 3' single-stranded extension comprising a sequence of at least 4 degenerate nucleotides that is random. The bottom strand also has a site-specific cleavable sequence or nucleotide at or near the junction between the double-stranded region and the single-strand extension, suitable for causing the removal of the single-strand extension by cleavage. The partially double-stranded polynucleotide molecule may be in a population of partially double-stranded polynucleotide molecules, wherein each polynucleotide in the population has a different sequence of at least 4 random degenerate nucleotides within its 3' single-strand extension. Polynucleotide molecules having a 3' single-stranded extension can be used as 3' adapters. The 3' adapters may optionally contain a blocking moiety at the 3' terminus of the bottom strand and/or a phosphorylated or pre-adenylated 5' terminus on the top strand.

Another embodiment provides an adapter suitable for an RNA library that includes a partially double-stranded polynucleotide molecule comprising a double-stranded region having a first nucleic acid strand and a second complementary nucleic acid strand, wherein: (i) the first and second strands are a portion of one polynucleotide molecule or comprise 2 polynucleotide molecules, (ii) the first nucleic acid strand optionally comprises one or more of a phosphorylated or pre-adenylated nucleotide at the 5' terminus; (iii) the second complementary strand has a nucleic acid sequence that extends 3' from the double-stranded region to form a single-stranded extension containing at least 4 degenerate nucleotides in a sequence; and (iv) a site-specific cleavable sequence or nucleotide at or near the junction between the double-stranded region and the single-strand extension, suitable for removing the single-strand extension by cleavage. The second complementary strand may optionally have a blocking moiety at the 3' terminus.

Another embodiment provides a population of 3' adapters as defined above, wherein the single-stranded extension containing at least 4 degenerate nucleotides in a sequence differs for each 3' adapter in the population.

In some embodiments, the top strand (or first strand) preferably comprises a pre-adenylated 5' terminus.

In some embodiments, the 3' single-stranded extension has a length in the range of 4-12 nucleotides and a site-specific cleavable sequence or nucleotide.

The site-specific cleavable sequence or nucleotide may include for example, a phosphorothioate, a dUMP, or a recognition sequence for one of a subset of restriction endonuclease characterized by having been modified so that it can only cleave one strand of a duplex (a nicking endonuclease). The bottom strand of the partially double stranded polynucleotide (3' adapter) may contain a phosphorothioate modification on the backbone of DNA, which can be cleaved by a phosphorothioate-specific restriction enzyme or chemical. Alternatively, the bottom strand of the 3' adapter can contain a uracil for cleavage by Uracil-DNA Glycosylase (UDG) and a glycosylase or glycosylase/lyase. Alternatively, the bottom strand of the partially double stranded polynucleotide or 3' adapter can contain a restriction endonuclease recognition site suitable for single-strand cleavage by a nicking endonuclease.

In some embodiments, the site-specific cleavable sequence or nucleotide is positioned at the junction of the single-stranded extension and the double-stranded region.

In some embodiments, the site-specific cleavable nucleotide or sequence or bond is positioned within the double-stranded region on the bottom strand (or second strand) within 8 nucleotides, preferably within 4 nucleotides of the junction of the single-stranded extension and the double-stranded region.

In some embodiments, there is more than one cleavable nucleotide or sequence in the polynucleotide molecule, wherein cleavable nucleotides or sequences are positioned in the double-stranded region on the bottom strand within 8 nucleotides of the junction of the single-stranded extension and the double-stranded region, preferably within 4 nucleotides from the junction.

In some embodiments, the blocking nucleotide on the splint adapter prevents ligation where the blocking nucleotide may include a modification selected from the group consisting of a 3' inverted dT, a 3' C3 spacer, a 3' amino dN, a 3' phosphorylated dN, and a dideoxynucleotide.

In one embodiment, a composition is provided that includes a 5' exonuclease such as a lambda 5' exonuclease and a nicking enzyme(s). The composition may include in addition to the 5' exonuclease, one or more of an enzyme selected from the group consisting of: a deadenylase, a nicking endonuclease, and/or a glycosylase/lyase or glycosylase.

In one embodiment, a method is provided that includes: ligating a randomized splint adapter as defined herein to a 3' end of a target RNA, where cleavage of the single-strand extension prevents adapter dimerization; and removing any residual dimers of the 3' adapter by adding a second composition that includes a 5' exonuclease and a deadenylase. Following removal of any residual dimers, the method may further comprise ligation of a 5' adapter.

Also provided is a kit. In some embodiments the kit may comprise (a) a partially double-stranded polynucleotide molecule for use as a 3' adapter as described herein; and (b) a second a partially double-stranded polynucleotide molecule suitable for use as a 5' adapter having the following features: a top strand and a bottom strand provided by the same or different polynucleotide molecules, wherein the top strand is complementary to a portion of the bottom strand to form a double-stranded region and the bottom strand comprises a 5' single-stranded extension that contains a sequence of at least 4 degenerate nucleotides. In some embodiments, the kit comprises a population of said second a partially double-stranded polynucleotide molecules, wherein the at least 4 degenerate nucleotide sequence is a random sequence that differs for each polynucleotide in the population.

In some embodiments, the kit may further comprise one or more enzymes selected from the group consisting of a ligase, a nicking enzyme, a glycosylase, a deadenylase, and an exonuclease.

The first and second polynucleotide molecules may be DNA or RNA. In one embodiment, the first partially double-stranded polynucleotide molecule (3' adapter) is DNA for ligating to the 3' end of a target RNA or DNA and the second a partially double-stranded polynucleotide molecule (5' adapter) is an RNA for ligation to the 5' end of the molecule. In one embodiment, the target polynucleotide is an RNA. In one embodiment the target polynucleotide is a library of RNA molecules, such that the adapter-ligated RNA library can be reverse transcribed and optionally amplified for sequencing by a sequencing platform. The kit may include instructions for use in methods that require a plurality of ligation steps involving a single-stranded target polynucleotide or a library of RNA molecules and 3' and 5' adapters for purposes related to at least one of characterization and quantification of the target polynucleotide. Examples of uses of the kit include: reducing background, which is exacerbated during amplification of a reverse transcript of an RNA; for sequencing reactions (for example NGS or Sanger sequencing); quantification and/or cloning; or other uses known in the art.

In one embodiment, a method is provided for ligating 3' adapters to single stranded target polynucleotide molecules, that includes combining any of the 3' adapter polynucleotide molecules described above with a population of target polynucleotide molecules to produce a reaction mix; incubating the reaction mix to ligate the 3' adapter polynucleotide molecule to the 3' target polynucleotide molecules in the population; and cleaving the polynucleotide molecule at the site-specific cleavable sequence or nucleotide so as to remove the degenerate sequence.

In one embodiment, a method is provided for ligating 3' adapters to RNA, that includes combining any of the 3' adapter polynucleotide molecules described above with a population of RNA molecules (target polynucleotides) to produce a reaction mix. This step of combining may further include the enzyme composition that includes the nicking enzyme and the 5' exonuclease and may further include a deadenylase. The method includes incubating the reaction mix to ligate the 3' adapter polynucleotide molecule to the 3' ends of the RNA molecules in the population; and cleaving the polynucleotide molecule at the site-specific cleavable sequence or nucleotide so as to remove the degenerate sequence. In one embodiment, the cleavage is performed with an enzyme, where the enzyme may be a nicking endonuclease, glycosylase or glycosylase/lyase.

In a further embodiment, the method includes adding a 5' polynucleotide adapter molecule as defined herein, having a 5' single-strand extension comprising degenerate nucleotides, to the product of the method defined above to produce a second reaction mix; and incubating the second reaction mix to ligate the 5' polynucleotide adapter to the 3' adapter ligated RNA molecules in the population.

In some embodiments, the steps of the method may be performed in a single reaction vessel.

In some embodiments, no intermediate purification or separation steps are performed between the method steps.

In some embodiments, the method may further comprise incubating the adapter-ligated product of the method with a reverse transcriptase, to copy the ligated RNA into complementary DNA (cDNA). In these embodiments, cDNA synthesis may be primed using the bottom strand of the polynucleotide molecule, after the 3' single-stranded extension has been cleaved.

In some embodiments, high adapter ligation yield and reduced bias does not vary significantly for other populations of RNA.

In some embodiments, the target RNA molecules in an RNA library are variable in size and concentration.

In any of the above embodiments, reference to the "top" strand is intended to include a reference to the first strand, and reference to the "bottom" strand is intended to include reference to the second strand. Also reference to "degenerate nucleotides" in the polynucleotide molecule refers to a sequence of at least 4 nucleotides, wherein the at least 4 degenerate nucleotide sequence is a random sequence that differs for each polynucleotide in a population of polynucleotides. The nucleotides in the degenerate sequence may be selected from A, G, U, T, C and modifications and analogs thereof that may be naturally occurring or unnatural chemical analogs.

BRIEF DESCRIPTION OF THE FIGURES

The figures and drawings are intended to illustrate one or more versions of the compositions and/or methods described herein. Unless stated otherwise, these are not intended to be limiting for the purpose of interpreting the scope of any claims.

In FIG. 3A the single-strand extension is "cut before" the second ligation while in FIG. 3B, the single-strand extension on Adapter 2 and 1 are cleaved after the two ligation events "cut after". In FIG. 3C and FIG. 3D, the 3' terminal nucleotide of the bottom strand of Adapter 2 is blocked (an optional feature for blocking any residual self ligation).

FIG. 9 shows some different forms of the 3' adapter (Adapter 2). "App" or "p" at the 5' terminus of the top strand is adenylation or phosphorylation, respectively. "X" is the site-specific cleavage site. "*" at the 3' terminus of the bottom strand is a blocking nucleotide.

DETAILED DESCRIPTION OF THE EMBODIMENTS

Figure 1:
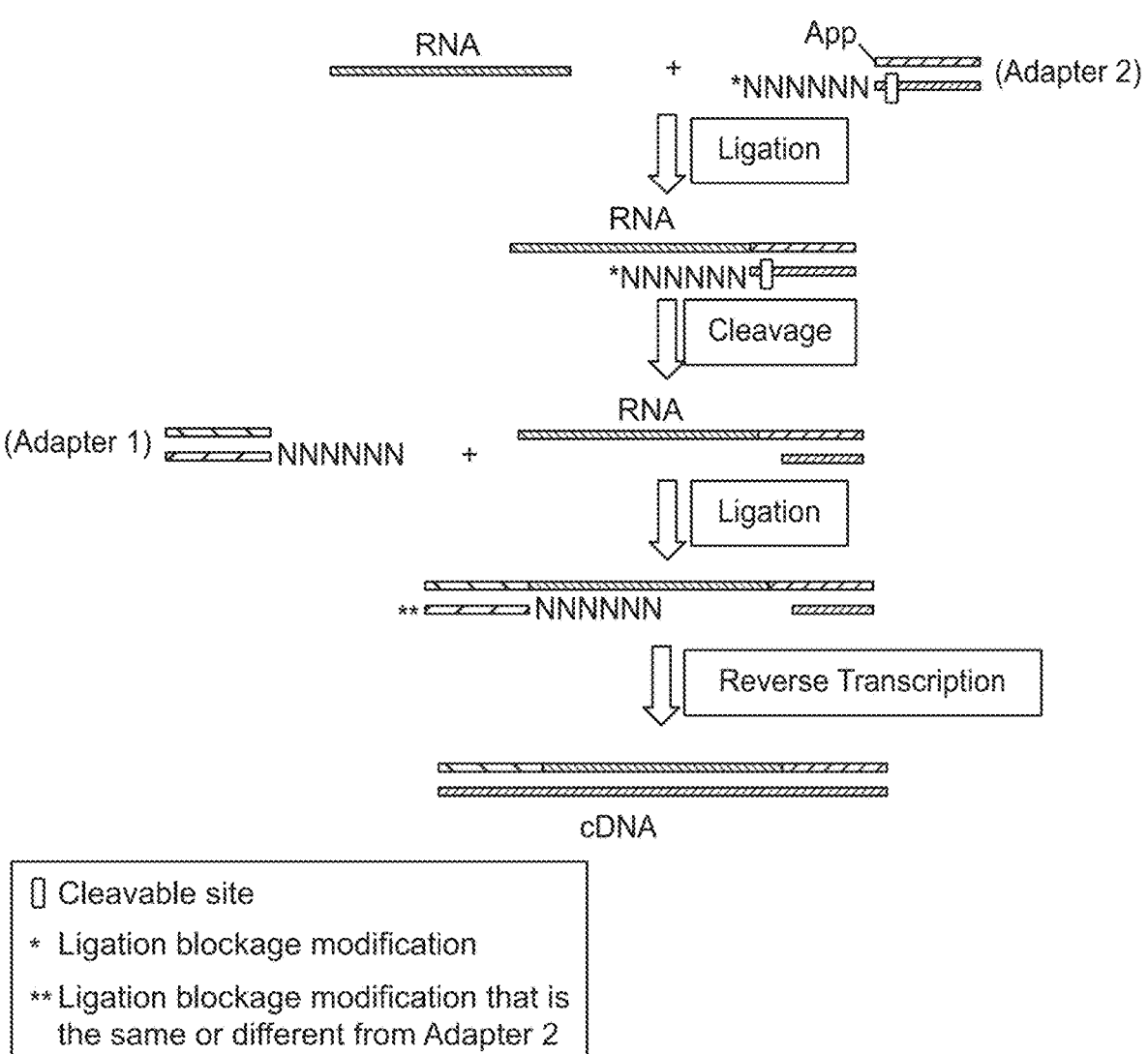
FIG. 1 shows a workflow in which polynucleotide adapter molecules can be added to both the 3' end (Adapter 2) and the 5' end of a target polynucleotide (Adapter 1), including nucleic acids that have unknown ends. This figure illustrates an example in which adapters are ligated to RNAs that do not have a polyA tail such as sRNAs and fragments of messenger RNA. In this example, the workflow involves four steps: (a) ligating one strand of a splinted double-stranded adapter that contains a 3' single-stranded extension (Adapter 2) to the 3' end of a target nucleic acid; (b) removing 3' single-stranded extension of the ligated adapter by cleavage of a site in the adapter and optionally preventing adapter dimers formation with an exonuclease; (c) ligating a strand of a double-stranded nucleic acid adapter that contains a 5' single-stranded extension (Adapter 1) to the 5' end of the target nucleic acid; (d) reverse transcribing the product of step (c) to produce cDNA that has adapter sequences at both ends; and (e) optionally PCR amplifying the adapter ligated polynucleotide (not shown) for generating a sequencing library. The 3' adapter as shown is characterized by a first top strand and a complementary bottom strand where the bottom strand includes a degenerate 3' single-strand extension and a one or more cleavage sites or linkers positioned on the bottom strand at the junction of the single-strand or double-strand regions or contained within the double-stranded region on the bottom strand near the single stranded region (for example within 4 nucleotides of the junction or no more than 8 nucleotides from the junction). Other features of the 3' adapter may include optionally a terminal adenylated diphosphate at the 5' terminus of the top strand and a modified terminal nucleotide on the 3' end of the bottom strand. The 5' adapter similarly has a top strand and a complementary bottom strand with the bottom strand having a 5' single-strand extension containing degenerate bases. Adapter 1 may also optionally have a ligation blockage modification that is the same or different from the modification on Adapter 2.

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise. As used herein, the articles "a", "an", and "the" relate equivalently to a meaning as singular or plural unless the context dictates otherwise.

The term "polynucleotide" refers to a DNA, RNA, chimeric DNA/RNA molecule, or a DNA strand hybridized to an RNA strand. The term "polynucleotide" as defined herein is used to describe the target and the adapters. Thus, any of the target polynucleotide, 3' adapter and/or 5' adapter may be a DNA, an RNA, or a DNA/RNA chimera or hybrid; and may contain one or more modified nucleotides, for example 2'O methyl NTP. In some embodiments, where the target polynucleotide is RNA, the 3' adapter is DNA and the 5' adapter is RNA; although optionally the 5' adapter may be DNA also. A "polynucleotide" as used herein may have one or more modified bases.

The target polynucleotide may be a single species derived from nature or may be synthetic or may be part of a population of polynucleotides whose members are derived from a cell or genome or other source. The target polynucleotide may be single-stranded intact sRNA or fragments of larger RNA molecules. The RNAs may be derived from nature or may be synthetic or may be part of a pool of different types of RNA. Sizes of target polynucleotides may range from 20 nucleotides in length to 10 kb or longer.

sRNAs include micro RNAs (miRNAs), PIWI associated RNAs (piRNAs), short interfering RNAs (siRNAs), endogenous short interfering RNAs (esiRNAs) and short hairpin RNAs (shRNAs), fragments of mRNA, viral RNA and structural RNAs like ribosomal RNA (rRNA), transfer RNA (tRNA) and 5S ribosomal RNA (5S RNA). Any or all these sRNAs can be ligated and amplified by this approach. There are no size or sequence requirements for the polynucleotide. However, the polynucleotide preferably has a free 3' OH to allow its ligation to the top strand of the 3' adapter.

The term "strand" as used herein refers to a nucleic acid made up of nucleotides covalently linked together by covalent bonds, e.g., phosphodiester bonds. Double-stranded DNA has two complementary strands of nucleic acid referred to herein as the "top" and "bottom" strands. The assignment of a strand as being a top or bottom strand (or any of the equivalent terms such as "Watson" and "Crick") is arbitrary and does not imply any particular orientation, function or structure.

The term "degenerate sequence" refers to a region of a polynucleotide in which any nucleotide can occur in preferably a random order. A degenerate sequence varies from polynucleotide to polynucleotide in a population of the polynucleotides. For instance, in a chemically synthesized oligonucleotide, a specific position in the oligonucleotide polymer could be specified to have any nucleotide incorporated. This is achieved by introducing a mixture of nucleotides (most often dA, dG, dC, dT for DNA oligonucleotides, and A, G, C and U for RNA oligonucleotides) during the stepwise chemical reactions that result in oligonucleotide chain elongation. A degenerate sequence may by described by the formula $N_{2-10}$ (e.g., $N_3$—$N_8$), where N corresponds to G, A, C, and T or U, or equivalent modified e.g. 2'O methylated nucleotides (2'O Me nucleotides). A polynucleotide that comprises "at least 4 degenerate nucleotides" thus comprises a sequence of 4 nucleotides, each of which may be N. The length of the degenerate sequence is at least 4, 5, 6, 7, 8, or 9 nucleotides. A degenerate sequence an also be described as a "random" sequence. A degenerate sequence comprises one or more (e.g., at least 2, at least 3, at least 4, at least 5, or 5 to 30 or more) nucleotides selected from R, Y, S, W, K, M, B, D, H, V, N (as defined by the IUPAC code). In other words, a degenerate sequence varies from molecule to molecule. In some, a degenerate sequence may be random (i.e., composed of a series of Ns, where N is represented by all four nucleotides in a population of molecules). An oligonucleotide having a degenerate sequence can be made by mixing together oligonucleotides of a defined sequence or by synthesizing an oligonucleotide such that a mixture of bases is added to one or more positions. The nucleotides in a degenerate sequence may be selected from A, U, G, T and C or modifications thereof or analogs thereof. Examples of modified nucleotides include methylated, hydroxymethylated, or glucosylated nucleotides. Other modifications include 8-oxoguanine and thymidine dimers. Also included are any known chemical modifications including naphthalene modified cytosine (see for example, U.S. Pat. No. 8,975,388) modified benzylguanine (see for example, U.S. Pat. Nos. 8,178,314, 8,163,479, and 8,227,602) and tagged nucleotides such as biotinylated nucleotides.

The term "ligating," as used herein, refers to joining of separate single-stranded polynucleotides to each other to form a single molecule. This is commonly but not exclusively achieved by means of a ligase. An RNA ligase can readily ligate a single-strand DNA to a single-strand RNA at the 3' end of the RNA. An RNA ligase can also readily ligate a 5' end of an RNA to a 3' end of an RNA. The ligation reactions described herein are generally achieved by means of a ligase such as available commercially and described in the New England Biolabs, Inc. catalog. Ligases include ATP-requiring RNA ligases such as a T4 RNA ligase 1 and T4 RNA ligase 2 such as T4 Ligase 2 truncated KQ or other mutants of T4 RNA ligase 2 as described in the examples and additionally include NAD requiring ligases such as Taq ligase. Another alternative ligase is *Chlorella* virus PBCV-1 ligase for splint ligation. Splint ligation may be achieved when 2 single-strand polynucleotide molecules anneal at proximate positions on a single complementary 'splint' molecule (single-stranded polynucleotide) and ligation occurs at the proximate ends of the two adjacent single-stranded polynucleotides.

Provided herein is a polynucleotide molecule that is a 3' adapter, also referred to herein as a randomized splint adapter, where the top strand of the adapter is suitable for ligating to the 3' end of a single-stranded target polynucleotide. In some embodiments, the 3' adapter may be used in conjunction with a 5' adapter to make a cDNA library from a population of RNA molecules. In some embodiments, the features of these adapters include, for the 3' adapter, a cleavable single-stranded degenerate sequence (which can be used as a "splint" during ligation) and blocking groups. When the adapters are ligated to a population of RNA molecules, the 3' adapter may be DNA while the 5' adapter may be RNA or a hybrid DNA/RNA, where the degenerate sequence is DNA. Individual adapters include the degenerate sequence on the bottom strand that is at least 4-10 or more nucleotides and preferably less than 100 nucleotides, less than 50 nucleotides, or less than 30 nucleotides in length.

The 3' adapter includes a double-stranded region that is composed of the first sequence of the top strand and the second sequence of the bottom strand. The double-stranded region should be of sufficient length to allow the first and second sequence to base pair with one another in solution. In some embodiments, the double-stranded region should be at least 6 bp in length, at least 8 bp in length, or at least 10 bp in length, but can be shorter in some cases. For example, the double stranded region may be in the range of 4-50 bp or 8-30 bp. The 5' terminus of the top strand may be phosphorylated or adenylated or have other chemical moieties on the 5' terminus that facilitates bimolecular ligation. No blocking group is necessary on the 3' end of the top strand. The 3' adapter molecule may have a blocking nucleotide on the 3' terminus of the bottom strand. Examples of a blocking nucleotide include, a modified deoxyribose or ribose sugar. In these examples, the 3' hydroxyl group is unavailable for further extension of the oligonucleotide by 3' to 5' phosphodiester formation. Examples of ligation blocking modifications include 3' inverted dT, 3' C3 spacer, 3' amino, 3' phosphorylation, and dideoxynucleotides. Generally, the modification prevents the 3' end from ligating, i.e., makes the 3' hydroxyl group unavailable for 3' to 5' phosphodiester bond formation.

The 3' single-stranded extension (the "splint" region) on the bottom strand (i.e., the third sequence) is joined to the double-stranded region by a junction region, which may be a nucleotide, linker or other sequence. The single-stranded extension of degenerate nucleotides that forms the splint has a length that is, e.g., at least 4 nucleotides, 5 nucleotides, 6 nucleotides, 7 nucleotides, 8 nucleotides or 9 nucleotides, although 6 nucleotides are exemplified in the figures. The sequence of the single-stranded region may vary in a pool of adapters used to create a single library. The amount of sequence variation may depend on, for example, the length of the degenerate sequence and the number of different nucleotides that are permitted at each position.

The 3' adapter design, that relies on among other features a degenerate single-strand extension to hybridize to unknown single stranded target sequences, enables a workflow that significantly reduces bias and increases yields, accuracy and sensitivity of sRNA sequencing from a population of sRNAs. This observed increase in ligation efficiency and/or reduction in ligation bias with 3' randomized splint adapters compared favorably with previously described single stranded adapters where significant bias in favor or against certain target sequences associated with single strand adapters was problematic in evaluating library content.

In one embodiment, the single-strand extension on the bottom strand of a DNA adapter is hybridized to a target single-strand RNA. Subsequent ligation of the 3' end of the target RNA and the 5' end of the top strand of the DNA adapter occurs to form a double-stranded region. The single-strand extension on the adapter is then removed by cleavage. Cleavage preferably occurs at a single site located at or within 5 or 8 nucleotides from the junction region between the double-strand and single-strand regions. In certain embodiments, 1 nucleotide or at the junction is preferable. For example, the cleavage site may be within the second sequence, up to 8 nucleotides (e.g., 1, 2, 3, 4, 5, 6, 7 or 8 nucleotides) 5' of the junction between the second and third sequences. A plurality of cleavage sites may be introduced into the bottom strand for the purpose of removing the single-strand extension, but one site is sufficient. The DNA adapter may be a 3' adapter for the target polynucleotide.

"Cleavage" refers to a site-specific cleavable sequence or nucleotide may include for example, a phosphorothioate, a dUMP, or a recognition sequence for the restriction endonuclease that is a wild type or has been modified to cleave on one strand only (a nicking endonuclease). Cleavage may also occur by chemical means or by photocleavable means or a mixture of these methods or other methods. Because the sequence that is 5' of the cleavage site may be used as a primer in the present method, cleavage results in a 3' hydroxyl group. Such a cleavage site is selectively cleavable in that it can be cleaved without cleaving other sites in the same molecule.

For example, the bottom strand of the 3' adapter described herein (e.g. Adapter 2 in FIG. 1) can contain a cleavage site selected from any of the aforementioned and can be cleaved accordingly.

In one example, the cleavable site is a single nucleotide (deoxyuridine), and the splint region is released using uracil deglycosylase and an AP endonuclease such as Endonuclease IV. In another example, the cleavable site is a sequence that can be specifically cleaved by a site-specific nicking endonuclease. The recognition sequence for this nicking endonuclease may be the same or different from the cleavage site in the double-stranded region of the adapter. The recognition site may be the same as the cleavage site where nicking occurs after a double-stranded molecule is formed between the splint and the target polynucleotide in the reaction mixture. The product of cleavage provides a 3' end for template-dependent polymerase reactions.

Cleavage of the adapter to remove the single strand extension as shown in FIG. 1 following ligation to the target RNA, may occur at the same time or can be preceded or followed by treatment of the ligated sample with an exonuclease that can degrade double-stranded DNA from the 5' end such as lambda exonuclease or Exonuclease V to remove any residual adapters from the sample. The addition of the exonuclease may further include addition of a deadenylase such as a pyrophosphatase such as tobacco acid pyrophosphatase or a pyrophosphohydrolase such as RppH.

For library construction as shown in FIG. 3A-3D, it may be desirable to use a 5' adapter in a second ligation step for ligation to the 5' end of the single-strand target polynucleotide. Example 8 provides one embodiment of the method for library construction after ligation of 3' and 5' adapters to sRNAs followed by reverse transcription and amplification.

The 5' adapter may be DNA but is preferably an RNA or an RNA/DNA hybrid. The 5' adapter comprises a double-stranded region having a top strand (RNA) and a bottom strand (DNA or RNA) with a single-stranded extension (the splint region) at the 5' end. In one embodiment, the single-stranded extension has a length of at least 4 nucleotides, at least 5 nucleotides, at least 6 nucleotides, at least 7 nucleotides at least 8 nucleotides or at least 9 nucleotides although 6 nucleotides are shown in the figures. However, for the 5' adapter, a specific junction nucleotide or sequence is not required, as cleavage of the splint region is not required; nor is a blocking nucleotide required at either end of the bottom strand, since ligation occurs only between the OH on the 3' end of the top strand of the 5' adapter and the phosphate on the 5' end of the RNA.

The 3' and 5' adapter molecules find utility for those reactions that require attachment of known sequences to both ends of a single-stranded target polynucleotide. The adapter sequences may contain a sample barcode, a unique molecular identifier, priming sites for amplification and sequencing, and/or modifications or labels such as biotin or other label known in the art which enhance separation or identification of adapter-target constructs.

The 3' adapter is suitable for template-switching workflows where the addition of a 5' adapter shown in FIG. 1 is substituted by a template switching step for preparing sequencing libraries. The attachment of a 3' adapter to the 3' end of any target RNA is particularly advantageous when the target RNA lacks a known 3' terminus such as a polyA tail. The 5' adapter can optionally be added by template switching.

In addition to providing a primer for reverse transcription, the 3' adapter may be used as an affinity tag to enrich for cell RNA against a background of DNA, protein, lipids, carbohydrates etc. By way of example, the 3' adapter may comprise an affinity tag, such as a biotin moiety, to enable enrichment of adapter-ligated molecules using e.g. streptavidin. The ligation of the 5' adapter to the 5' end and/or the 3' adapter at the 3' end of the RNA may facilitate sequencing the RNA directly using the Oxford Nanopore platform.

After the adapter sequences have been attached, the RNAs may be converted to cDNA; optionally amplified, and/or sequenced by a variety of methods. Alternatively, for sRNAs, the adapter ligated RNA may be sequenced directly, for example using an Illumina sequencing platform.

Present embodiments of adapter ligation enable manufacture of a cDNA using reverse transcriptase that have one or more of the following advantages: a one pot workflow; no purification steps required to produce a high yield of a sequencing library formed from an RNA population with reduced bias; consistency of performance; and suitability for single-stranded DNA and single-stranded RNA target polynucleotides having a wide range of sizes and a wide range of concentrations.

The method described herein can be employed to analyze RNA (particularly sRNAs, long non-coding RNAs or fragmented mRNA) from virtually any organism and/or sample-type originating from prokaryotes, eukaryotes, mycoplasma and archaea. Examples include, but are not limited to, microbes, plants, animals (e.g., reptiles, mammals, insects, worms, fish, etc.), tissue samples, cadaveric tissue, archaeological/ancient samples, etc. In certain embodiments, the RNA sample used in the method may be derived from a mammal, where in certain embodiments the mammal is a human. In exemplary embodiments, the RNA sample may contain RNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the RNA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free RNA (cfRNA) obtained from blood, e.g., from the blood of a pregnant female or a patient such as a cancer patient. In other embodiments, the sample may be a pathogenic organism, sample from a microbiome, a plant sample or a fungal sample where the RNA to be sequenced is diagnostic for a selected situation such as disease, barcode of life, or phenotype analysis in a population of a single species.

The adapters and their use in a library preparation process using randomized splint ligation resolves previous challenges reducing bias and sensitivity of sequencing associated with this ligation strategy. The workflow described herein is suitable for detecting differentially expressed sRNAs that are typically 18-33 nucleotides in length and have a fundamental role in transcriptional and post-transcriptional gene regulation. RNAs can be used diagnostically, for many purposes, for example, tumor and matched normal tissues analysis where tumor cells express micro RNAs differently from matched normal tissue. sRNAs based RNA silencing regulates a wide variety of biological processes including development, maintenance and determination of cell fate, fine tuning of gene expression, silencing of transposons and antiviral defenses. tRNA fragments are a newly discovered and important class of sRNAs. The randomized splint ligation-based workflow described herein can reduce bias and increase the sensitivity of sRNA sequencing for a wide variety of target RNAs such as sRNAs that typically associate with members of the Argonaut protein family to form ribonucleoprotein complexes and act as guides for targeted RNA silencing through complementary base pairing. The randomized splint workflow is also effective for large RNAs and DNA allowing for highly accurate RNA and DNA sequencing.

Examples of sRNAs include for example, 2'OMe modified RNA, small interfering RNAs, tRNA derived fragments, piwi interacting RNA, plant miRNA, pseudouridine modified RNA. Transfer tRNA fragments (tRFs) are organized into two main categories: longer tRNA-halves and shorter tRNA fragments. Longer 3' and 5' tRNA-halves have a role in regulating protein synthesis and their biogenesis is triggered by cellular stress such as infection, oxidative or nutritional stress (Keam, et al., (2015) Life, 5, 1638-1651). Less is known about shorter 3'-tRFs and 5'-tRFs. However it has been shown that they can be loaded onto Argonauts and guide mRNA silencing on a variety of targets using mechanisms similar to miRNA induced silencing (see for example, Kumar, et al., (2014) BMC Biology, 12, 78; Shigematsu, et al., (2015) Gene Regul Syst Bio, 9, 27-33).

Typically, sRNAs associate with members of the Argonaut protein family to form ribonucleoprotein complexes and act as guides for targeted RNA silencing through complementary base-pairing 1. sRNA based RNA silencing regulates a wide variety of biological processes including development, maintenance and determination of cell fate, fine tuning of gene expression, silencing of transposons and antiviral defenses. Furthermore, aberrant expression of sRNAs is involved in many human diseases. miRNAs in particular are often aberrantly expressed in tumor cells and are useful biomarkers for both diagnosis and prognosis in a variety of cancer types (Bottani, et al., (2019) Journal of Clinical Medicine, 8, 1661).

Figure 9:
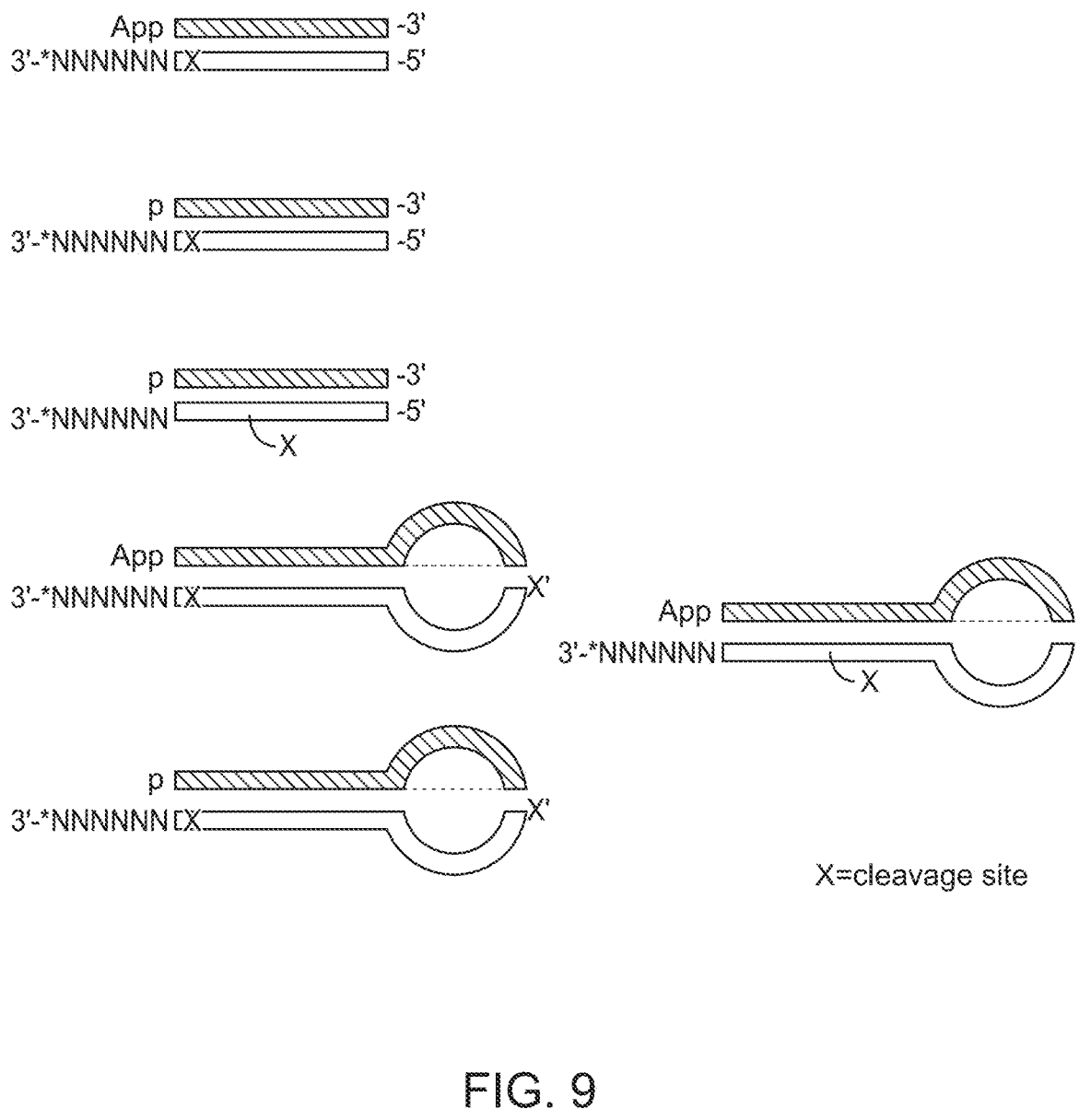

Also provided by this disclosure is a kit for practicing the subject method, as described above. A subject kit may contain at least a 3' adapter of the invention (e.g. as described in FIG. 9). The kit may further comprise a 5' adapter as described above; and/or the kit may also contain one or more enzymes, such as a ligase, a deadenylase, a glycosylase/lyase, and/or a nicking endonuclease.

The kit may include instructions for use in methods that require a plurality of ligation steps involving a single-stranded target polynucleotide and 3' and 5' adapters for purposes related to at least one of characterization and quantification of the polynucleotide. Examples of uses of the kit include sequencing of sRNAs (21-23 nucleotides) that are used by cells in genome regulation and can also be used as biomarkers. Other uses include sequencing RNA fragments in blood. sRNA molecules can be sequenced directly by Illumina sequencing platforms and do not require reverse transcriptases for analysis. Because the RNAs are small, there is no suitable internal location for priming synthesis of complementary strands, hence the adapters provide external priming sites for this purpose.

Examples of uses of kit include reducing background, which is exacerbated during amplification of a reverse transcript of an RNA, for sequencing reactions (for example NGS or Sanger sequencing), quantification and/or cloning or other uses known in the art.

The components of the kit may be combined in one container, or each component may be in its own container. For example, the components of the kit may be combined in a single reaction tube or in one or more different reaction tubes. Further details of the components of this kit are described above. The kit may also contain other reagents described above and below that are not essential to the method but nevertheless may be employed in the method, depending on how the method is going to be implemented.

Reagents provided in kits may also be provided in com-partmentalized cassettes or microfluidic devices or in a format suitable for multi-sample fluid handlers involving multi-well plates or other formats. sRNA libraries can provide biological markers for diagnosis of pathological states such as cancer in patients. Embodiments of the present methods can contribute to improving diagnosis in at least two ways.

In a first approach, for example, population analyses may be performed to characterize "normal" sRNAs that charac-terize a healthy person. This requires large numbers of libraries each from a different individual with computational analysis that involves machine learning. Processing these libraries to discover biomarkers that indicate pathogenicity in a population requires many additional samples from patients with characterized abnormal phenotypes.

In a second approach, patients who visit a doctor's office for an individualized diagnosis may provide a sample of blood that is sent to a testing laboratory or handled on site perhaps in the form of a microfluidic device where sRNA library is constructed with the present methods. The library is then sequenced in-sequencing instrument such as MiSeq® sequencer (Illumina, San Diego, CA). The patient sRNA profile is then compared to a database of sRNA population data to facilitate diagnosis.

In both scenarios, 3' adapters and then 5' adapters as described herein are ligated sequentially onto each of the sRNAs from a single patient or a population of patients where at least the 3' adapter or 5' adapter or both contain a sample bar code. These libraries can then be combined into a single pool either before or after PCR amplification step. Analysis of pooled libraries can then be performed followed by sequencing by MiSeq or other sequencing platform. Computational analysis of the profile of various sRNAs in a population from a single patient with a comparison of patient data with data from a "normal" population can reveal what type of cancer or other condition the patient might have and what sort of treatment regimen might be appropriate.

In embodiments of the invention, the polynucleotide described herein having a top strand and a bottom strand are not naturally-occurring.

The term "non-naturally occurring" refers to a nucleic acid that contains: (a) a sequence of nucleotides that is different to a nucleic acid in its natural state (i.e. having less than 100% sequence identity to a naturally occurring nucleic acid sequence); (b) one or more non-naturally occurring nucleotide monomers (which may result in a non-natural backbone or sugar that is not G, A, T or C); and/or (c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: (a) a combination of components that are not combined by nature, e.g., because they are at different locations, in different cells or different cell com-partments; (b) a combination of components that have relative concentrations that are not found in nature; (c) a combination that lacks something that is usually associated with one of the components in nature; (d) a combination that is in a form that is not found in nature, e.g., dried, freeze dried, crystalline, aqueous; and/or (e) a combination that contains a component that is not found in nature. For example, a preparation may contain a "non-naturally occur-ring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

All publications, patents, and patent applications men-tioned in this specification including U.S. Provisional Appli-cation No. 62/839,191 filed Apr. 26, 2019 and U.S. appli-cation Ser. No. 16/796,113 filed Feb. 20, 2020 are herein incorporated by reference to the same extent as if each individual publication, patent, or patent application was specifically and individually indicated to be incorporated by reference.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

All enzymes, if not stated otherwise, are from New England Biolabs, Inc. (Ipswich, MA). The manufacturer instructions were followed unless stated otherwise.

Example 1: Splint Ligation for Generating an RNA Sequencing Library in a Single Reaction Vessel In this example, the input RNA was a pool of microRNAs that contained 962 synthetic miRNA with equimolar con-centration (the MiRXplore™ library from Miltenyi Biotec, (Auburn, CA)). All total RNA samples were obtained from BioChain, Inc. (Newark, CA). All oligonucleotides were synthesized by Integrated DNA Technologies, Inc. (Coral-ville, IA). A DNA adapter was first ligated to the 3' end and then an RNA adapter was ligated to the 5' end of each input RNA in the pool using the workflow shown in FIG. 1 to form a sequencing library. The 5' RNA adapter (double-stranded molecule with 5' single-stranded extension) could be substituted with an RNA hybrid, in which the RNA is the top strand suitable for hybridization to the 5' end of the target RNA using T4 RNA ligase and the bottom strand could be DNA or RNA.

To reduce the secondary structure of input RNA, the RNA was heated to 70° C. and then rapidly cooled down on ice. The input RNA (pooled miRNA) (50 fmol) was then ligated to the 3' adapter (Adapter 2) using T4 RNA Ligase 2, Truncated KQ (NEB M0373) by incubating the reaction mix for 1 hour at 25° C. The bottom strand of Adapter 2 was cleaved at the deoxyU with UDG (NEB M0280) and Endonuclease IV (NEB M0304). The 5' adapter (Adapter 1) was then added to the reaction and ligated to the 5' end of target RNA with the T4 RNA ligase 2. ProtoScript® II Reverse Transcriptase (NEB M0368) was then added to the reaction mix to elongate the bottom strand of Adapter 2 to form the cDNA. Resulting cDNA was then purified using NEBNext® Sample Purification Beads (NEB E7767). The purified cDNA was PCR amplified with Q5® DNA Polymerase (NEB M0491). The PCR products were purified with NEBNext Sample Purification Beads (NEB E7767). The yield of the library was determined by 2100 Bioanalyzer® (Agilent, Santa Clara, CA). The sequencing of the library was performed on MiSeq or NextSeq® platform (Illumina, San Diego, CA).

2.5 pmol was used for the 3' adapter and subsequently 5 pmol was used for the 5' adapter.

The sequences of the 3' and 5' adapters are as follows:

```
3' adapter: Adapter 2:
Top strand:
                                   (SEQ ID NO: 1)
/5 App/AGA TCG GAA GAG CAC ACG TCT /3InvdT/

Bottom strand:
                                   (SEQ ID NO: 2)
AGA CGT GTG CTC TTC CGA TC/ideoxyU/(N1:25252525)

(N1)(N1) (N1)(N1)(N1)/3InvdT/

5' adapter: Adapter 1
Top strand:
                                   (SEQ ID NO: 3)
rGrUrUrCrArGrArGrUrUrCrUrArCrArGrUrCrCrGrAr CrGrArUrC Bottom strand:
                                   (SEQ ID NO: 4)
(rN1:25252525)(rN1)(rN1)(rN1)(rN1)(rN1)rGrArUrCrGr UrCrGrGrArCrUrGrUrArGrArArCrUrCrUrGrArArC
```

Adapter 1 and 2 were synthesized by IDT (Coralville, IA).

Where preadenylation was used, the 3' and 5' adapters were resuspended in annealing buffer (50 mM NaCl, 10 mM Tris HCl, 0.1 mM EDTA, pH 7.5). The adapter strand of the 3' adapter was pre-adenylated using the 5'DNA Adenylation Kit (NEB E2610) and purified using the Monarch® DNA Cleanup Kit (NEB T1030).

Reverse transcription was performed by adding 50 mM final concentration of Tris-HCl buffer (pH 7.5), 75 mM final concentration of potassium chloride, 10 mM final concentration of DTT, 500 μM final concentration of each DNTP, 20 units of Murine RNase Inhibitor (M0314), 200 units of ProtoScript II Reverse Transcriptase (NEB M0368) and nuclease free water to bring the final volume to 50 μL. This reaction was then incubated for 1 hour at 42° C. First strand cDNA products were purified using 70 μL NEBNext Sample Purification Beads (NEB E7767) and 70 μL of 100% Isopropanol. Reactions were washed and eluted in 10 μL of nuclease free water according to the manufacturer's directions (also see FIG. 1).

PCR amplification of the library was performed using NEBNext High-Fidelity 2×PCR Master Mix (NEB M0541) and 25 pmol each of the forward and reverse primers. PCR was performed with the following program: An initial denaturation of 98° C. for 30 seconds followed by a varying number of cycles depending on input of: 98° C. for 10 seconds, 62° C. for 30 seconds and 72° C. Followed by a final elongation step of 72° C. for 5 minutes. Libraries were size selected using the NEBNext Sample Purification Beads (NEB E7767) and using the Small RNA Library Size selection protocol from the NEBNext Small RNA Library Kit (NEB E7330). Purified libraries were assayed on the Agilent 2100 Bioanalyzer to assess purity and concentration before being pooled and sequenced using 50 cycles of single-end Illumina sequencing.

Figure 2:
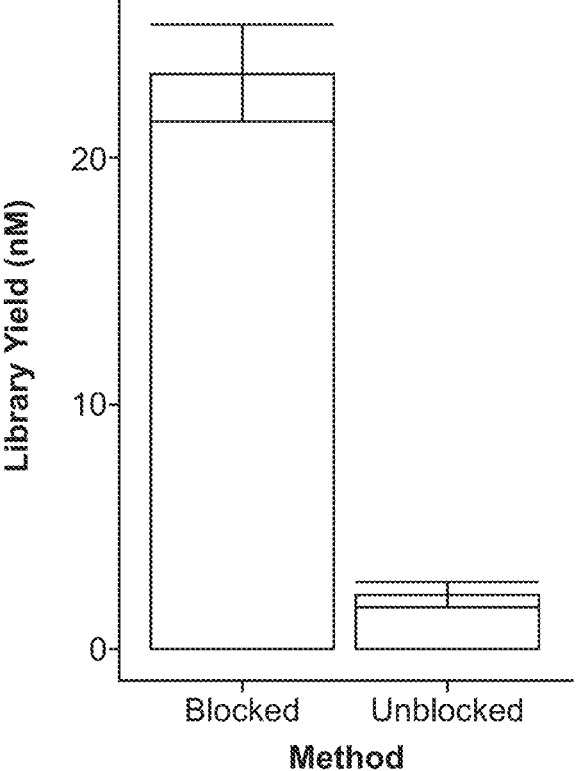
FIG. 2 shows that library yield is enhanced by the workflow exemplified in FIG. 1, where the 3' end of the bottom strand of the 3' adapter (Adapter 2) is blocked from ligation by a modified nucleotide.

To evaluate the effect of a blocking modification on the 3' end of the bottom strand of Adapter 2, an inverted dT blocking group was added. The control was unmodified (Adapter 2 obtained from IDT). This adapter was used according to the method above resulting in an enhancement of the library yield. The library yield using the blocking nucleotide was 10 times more than the one without blocking modification (see FIG. 2).

Figure 5:
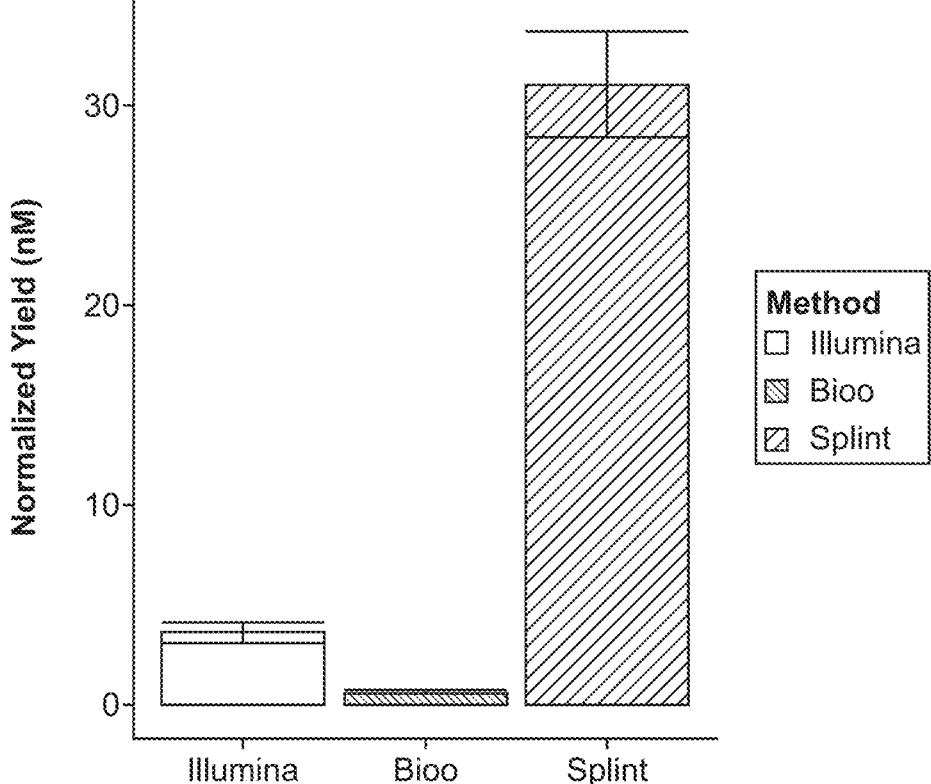
FIG. 5 shows that the yield of RNA represented in a library using the workflow in FIG. 1 (randomized splint ligation) is significantly greater than the yield provided by commercially available methods from Illumina and Bioo Scientific that uses single-strand adapters.
Figure 6:
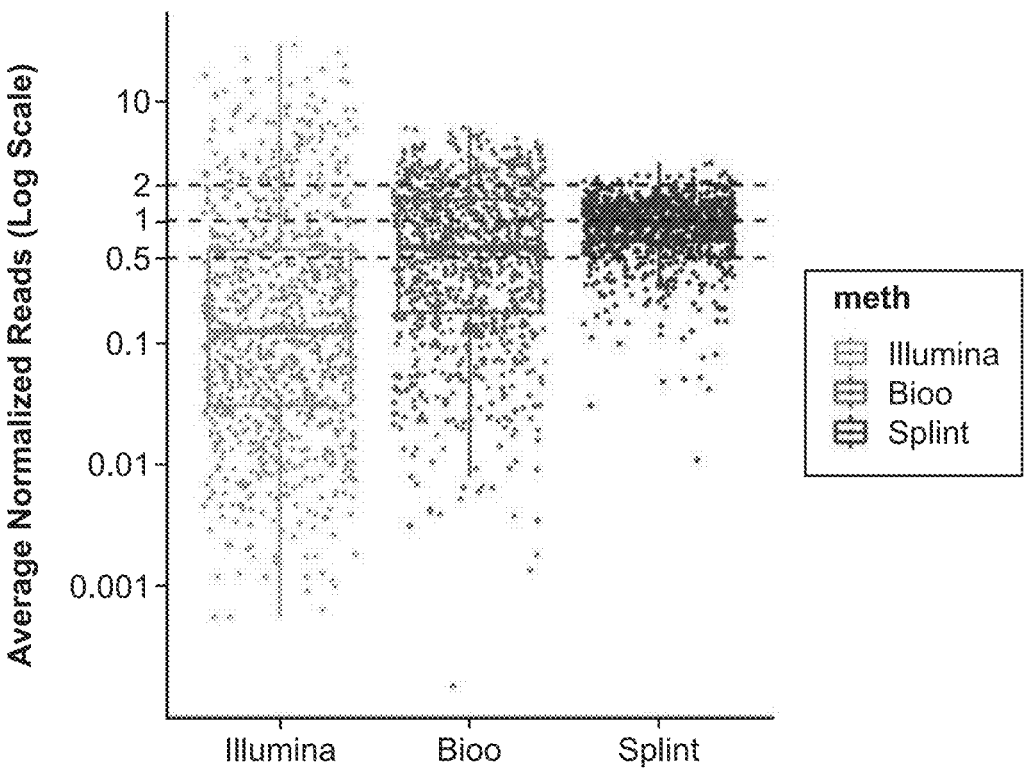
FIG. 6 shows that there is a significant reduction in bias using the workflow described in FIG. 1 using randomized splint adapters compared to the commercially available methods that rely on single-strand adapters.

Example 2: Splint Ligation Generates Improved Library Yield from Human Brain Total RNA Three different methodologies were compared for constructing RNA libraries using the same amount of starting material (500 ng of human brain total RNA). These were (1) Illumina TruSeq® Small RNA Library Preparation Kits (RS-200-0012, Illumina, San Diego, CA), (2) Bioo Scientific NEXTflex® Small RNA-seq Kit V3 (NOVA-5132-05, Bioo Scientific, Austin, TX), and (3) the splint ligation-based RNA library preparation method described in Example 1. Libraries were made according to the manufacturer's instructions. Library yield was assessed with the Bioanalyzer. Data shown is the average of 6-8 technical replicates. The yield was normalized to 9 PCR cycles. As a result, the splint ligation-based RNA library preparation method generates higher yield than both Illumina and Bioo Scientific's methods (see FIG. 5).

Figures 3A, 3B:
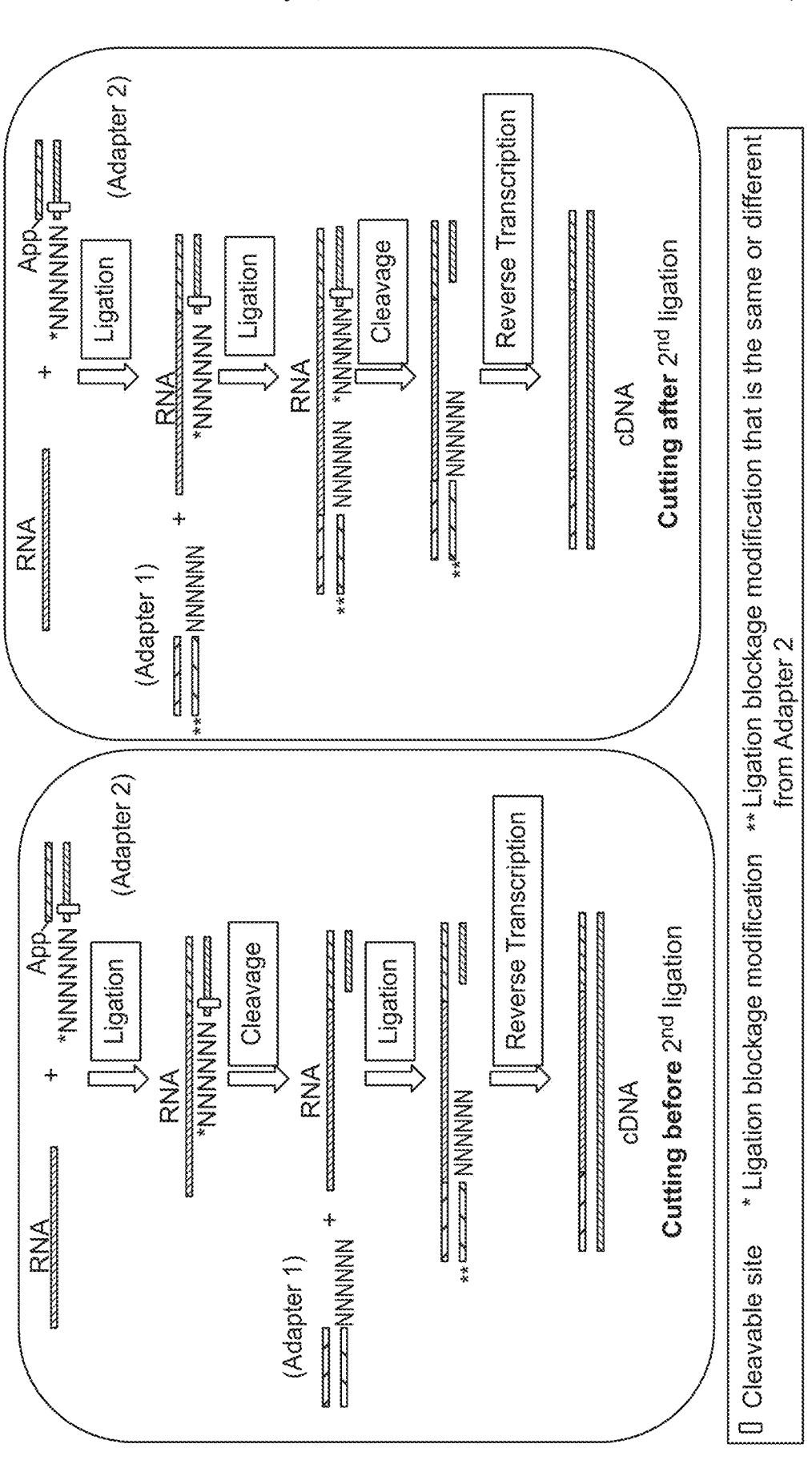
FIG. 3A-3B shows a schematic representation of workflows that requires cleavage of the 3' single-strand extension at different stages in the two workflows.
Figures 3C, 3D:
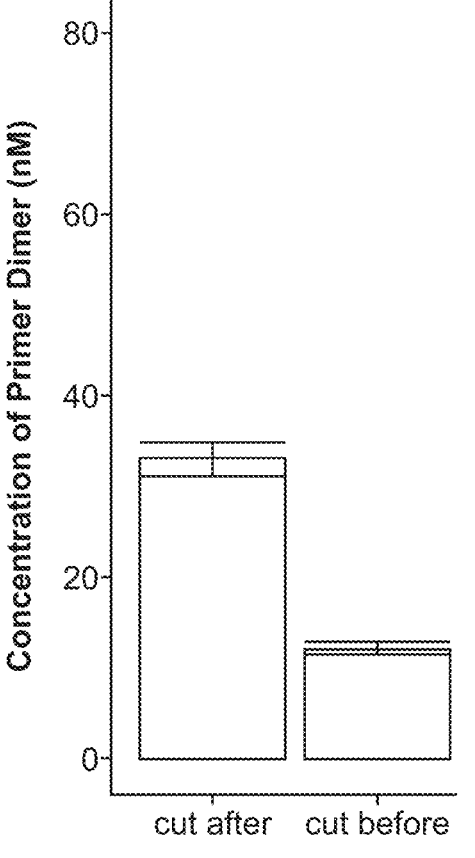
FIG. 3C-3D show effects on adapter dimerization (FIG. 3C) and yield of 3' adapter ligated RNA (FIG. 3D) of the different workflows. The results show that cleavage of the single-strand extension before the second ligation of the 5' end of the target RNA reduces adapter-dimer formation (FIG. 3C) and increases library yield (FIG. 3D) compared with after.

Example 3: To Demonstrate the Benefit of Cleaving the 3' Single-Strand Extension on the 3' Adapter Before the Second Ligation Step RNA libraries were generated as described in Example 1 where the cleavage site in the 3' adapter was deoxyuridine with cleavage using USER® (NEB M5505) to remove the single-strand extension on the bottom strand. Input RNA: 50 fmol of miRXplore input RNA and 2.5 pmol Adapter 2 were ligated. Cleavage was done before the second ligation ("cut before") or after the second ligation ("cut after") in which 5.0 pmol Adapter 1 was ligated to the 5' end of the RNA. The results are shown in FIG. 3C. Where USER cleavage was performed before the second ligation, primer dimer formation was decreased while the target miRNA yield was enhanced, when compared with USER cleavage after the second ligation. When the resulting libraries from the two methods were compared, cleavage before the second ligation resulted in a target to adapter dimer ratio of 7:1, whereas cleavage performed after the second ligation produced a ratio of 1.5:1 target to adapter dimer (FIG. 3C) demonstrating the advantages of cleavage of the single-strand extension prior to the second ligation step.

Figure 4:
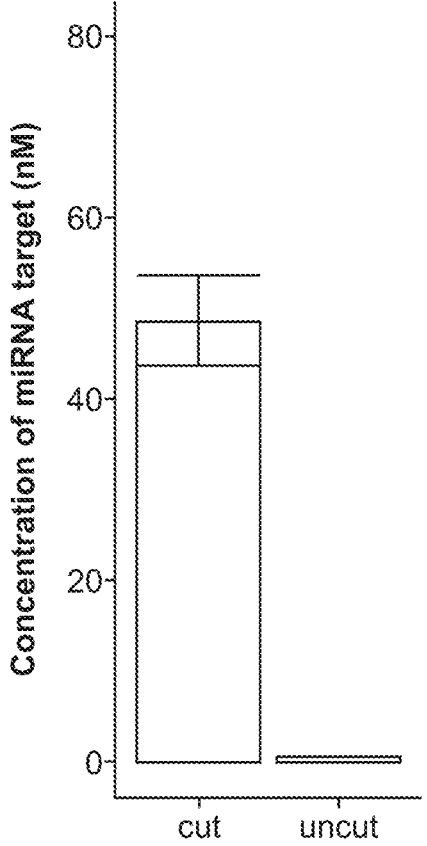
FIG. 4 shows that when a nicking restriction endonuclease (Nt.BsmAl in this example) cleaves the single-stranded extension from the 3' randomized splint adapters after the first ligation step, the concentration of adapter ligated target miRNA represented in a library increases compared with use of randomized splint adapters absent cleavage.

Example 4: To Demonstrate Improved Yield after Cleavage of the Single-Strand Extension Compared with No Cleavage In this example, a nicking endonuclease cleavage site was located in the bottom strand of Adapter 2 with a nicking endonuclease recognition sequence in the double-stranded region of the adapter to remove the single-strand extension on Adapter 2 after ligation. The bottom strand of Adapter 2 was designed to contain a BsmAI nicking site for cleaving the single-strand extension. Libraries were made according to the method in Example 1 where 50 fmol of miRXplore were ligated with 2.5 pmol Adapter 2 followed by cleavage with 5U Nt.BsmAI (NEB R0121), identified in FIG. 4 as "cut" and in the absence of cleavage as "uncut". Subsequently 5.0 pmol Adapter 1 was added to the mixture and ligated to the 5' end of the RNA-adapter conjugate. The yield of RNA library was substantial with the nicking enzyme cleavage, while there were almost no libraries formed in the absence of cleavage of the single-strand extension (FIG. 4).

Figure 7:
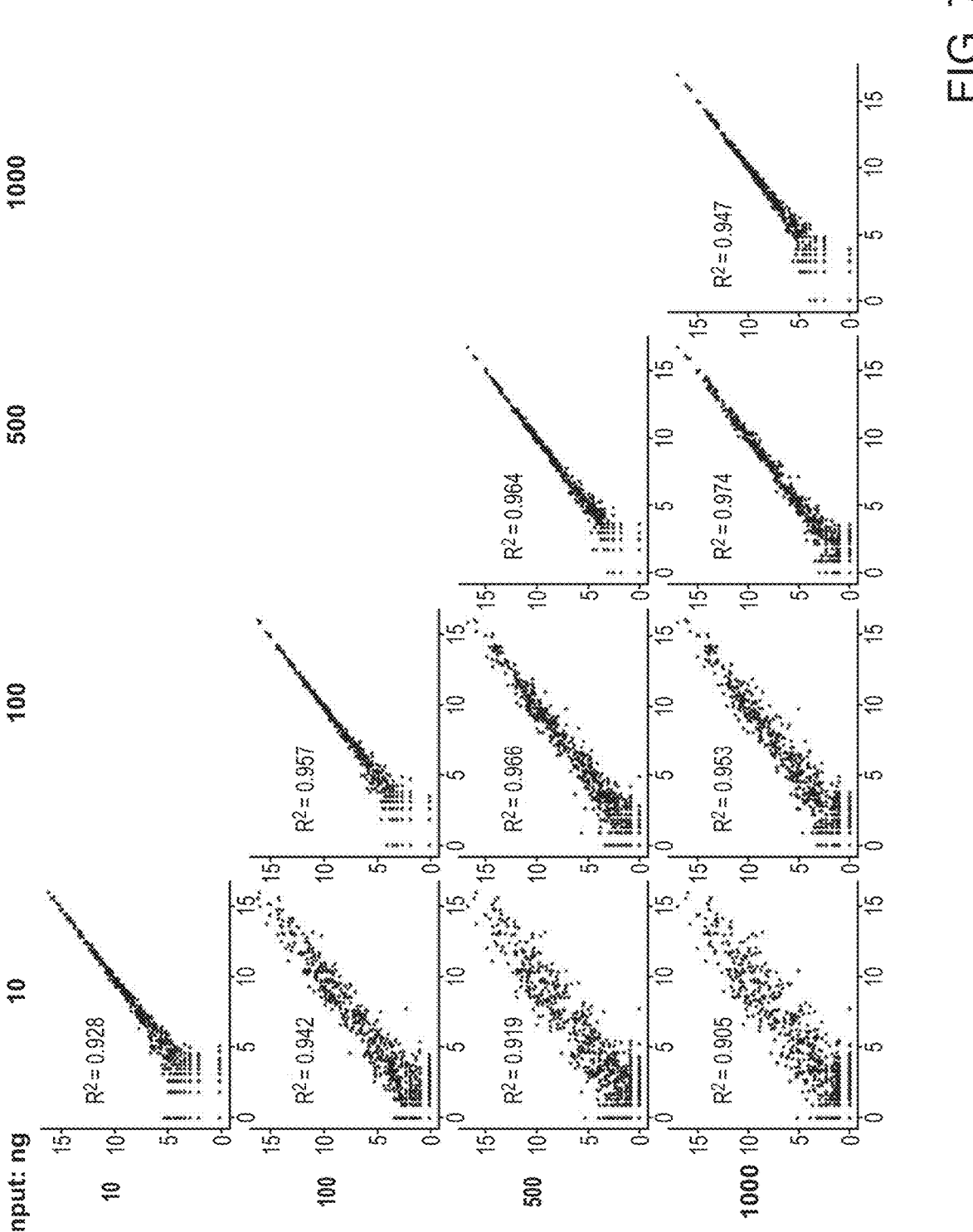
FIG. 7 shows that the workflow in FIG. 1 provides consistent performance over the range of RNA concentrations tested (in the range of 10 ng-1000 ng target RNA sample).

Example 5: Sequencing the Libraries of mcroRNA Showed Reduction of Bias Compared Commercial Kits Sequencing libraries were generated from 50 fmol input of miRXplore Universal Reference RNA as described in Example 1 with three different workflows described in Example 2 to determine the extent of unwanted bias from the adapter ligation reaction. Libraries were sequenced on the Illumina MiSeq in single end mode for 50 cycles to a read depth of greater than 2 million reads per library. Each library was sequenced in duplicate. Datasets were then randomly down-sampled to a depth of 2 million reads for analysis. After adapter trimming, reads were counted by mapping them to the reference sequences provided by the manufacturer. Reads were normalized by dividing the total number of mapped reads in each library by 962 to give an expected read count per miRNA species. Then the read count for each miRNA was divided by the expected read count to give a normalized read count. An miRNA that is present in the expected amount will have a normalized read count of one. Overrepresented sequences will have a normalized read count greater than one and underrepresented sequences will have a normalized read count less than one. Reads were plotted on a log scale. All analysis was done using the BBTools package (https://jgi.doe.gov/data-and-tools/bbtools/). The library generated with the Illumina workflow had the largest bias consisting of a large number of reads that are underrepresented. The library formed using the Bioo Scientific method workflow also showed has a large bias. On the other hand, the splint ligation method has the smallest bias (FIG. 7).

The bias was quantified by the percentage of miRNA sequences that are within 2-fold of the expected value of 1. Sequencing libraries made with the Illumina Kit quantify only 20% of the miRNAs within 2-fold of the expected value, while the Bioo Scientific Kit had 38.3% and the splint ligation method had 84.3% (FIG. 7).

Example 6: The 3' Adapter Ligation Workflow is Consistent for a Wide Range of Input RNA Concentrations Libraries were prepared from 1000, 500, 100 and 10 ng input of total human brain RNA (single healthy male donor, BioChain, Newark, CA). Library preparation protocol was stated in Example 1 and was identical for each input level, except for the following changes: Both adapters were diluted for the lower input levels (10-fold for the 100 ng input and 100-fold for the 10 ng input). In addition, the number of PCR cycles was varied according to the RNA input amount (10, 11, 14 and 18 cycles for the 1000, 500, 100 and 10 ng input levels respectively).

For 1000 ng and 500 ng of input RNA, 2.5 pmol was used for the 3' adapter and subsequently 5 pmol was used for the 5' adapter. For 100 ng of input RNA, the adapters were diluted 1:10 (0.25 pmol for the 3' adapter and 0.5 pmol for the 5' adapter). For 10 ng, the adapters were diluted 1:100 (25 fmol for the 3' adapter, 50 fmol for the 5' adapter).

Libraries were sequenced in duplicate on an Illumina MiSeq in single end mode for 50 cycles and down-sampled to a read depth of 2 million. Reads were mapped to the human genome (build GRCh38) using the STAR aligner and quantified using the standard Encode pipeline. Read counts were then log transformed and correlated across input amounts in R (R-project.org) using standard linear regression. The splint ligation-based RNA library preparation methods show consistent performance across different RNA input. Even for the comparison between 10 ng and 1000 ng, the $R^2$ value is more than 0.9, suggesting a high correlation and reflecting a consistent performance of the method across a wide range of input (FIG. 7).

Figure 8:
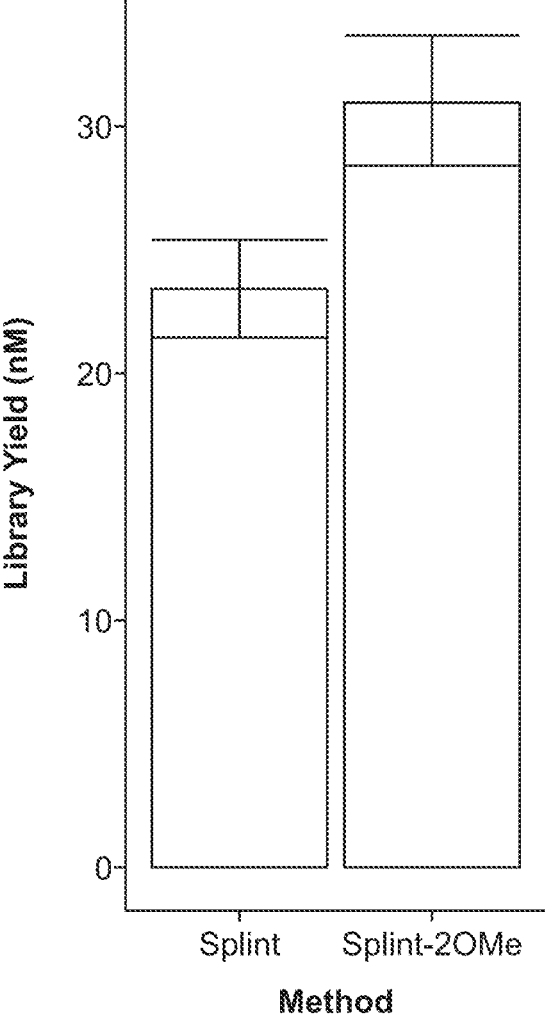
FIG. 8 shows that the performance of the workflow in FIG. 1 can be further enhanced by the substitution of A/G/T and C by 2-Ome A/G/T/C in the degenerate sequence of the 5' single-strand extension of the 5' adapter.

Example 7: Splint Ligation can be Further Improved by Substituting NTP with 2'O Me Nucleotides in the 5' Adapter Single-Strand Extension The 6 degenerate nucleotide region of bottom strand of the 5' adapter (Adapter 1) was designed to contain 6×2'O Me nucleotides (SEQ ID NO:3). (IDT) Libraries were made according to Example 1 with 500 ng of total human brain RNA (input RNA), 2.5 pmol Adapter 2 and 5.0 pmol Adapter 1. The yield obtained with modified Adapter 1 was compared with normal Adapter 1. The results showed that the modified nucleotides caused an increase in the library yields (FIG. 8).

```
3' Adapter 2:
Top strand:
                                    (SEQ ID NO: 1)
/5 App/AGA TCG AAG GAG CAC ACG TCT/3InvdT/

Bottom strand:
                                    (SEQ ID NO: 2)
AGA CGT GTG CTC TTC CGA TC/ideoxyU/(N1:25252525)

(N1)(N1)  (N1)(N1)(N1)/3InvdT/

5' Adapter 1
Top strand:
                                    (SEQ ID NO: 3)
rGrUrUrCrArGrArGrUrUrCrUrArCrArGrUrCrCrGrArCrGrArU
rC
```

-continued

Modified bottom strand:

(SEQ ID NO: 5)
(mN1:25252525)(mN1)(mN1)(mN1)(mN1)(mN1)rGrArUrCrGr

UrCrGrGrArCrUrGrUrArGrArArCrUrCrUrGrArArC/3InvdT/

Example 8: Library Construction Using Splint Ligation can be Further Improved by the Addition of Lambda Exonuclease and a Deaminase 50 fmol of synthetic miRXplore RNA, or 500 ng of total RNA was used as input to the libraries. Libraries were constructed with NEBNext, NEXTflex and TruSeq kits following the manufacturer's directions. The preferred ratio of RNA to adapters was 1:5 to 1:10. Where the amount of RNA in a sample was unknown, a titration was carried out. Based on initial testing PCR cycles were adjusted so that all libraries would be amplified to approximately the same concentration, which generally entailed amplifying the libraries made with the randomized splint method 2-3 cycles less than commercial kits using single strand adapters. Randomized splint ligation libraries were constructed using the following method. The following components were added to total RNA: 1× final concentration of T4 RNA ligase buffer (NEB M0204), 20% final concentration of PEG (NEB M0204), 0.05% final concentration of Tween 20 (VWR Radnor, PA), 2.5 pmol annealed 3' adapter (2.5 pmol top strand, 5 pmol bottom strand), 200 units of T4 RNA Ligase 2, truncated KQ (NEB M0373). These reactions were incubated in a thermocycler at 25° C. for 1 hour. Following ligation, 2.5 units of lambda exonuclease (NEB M0262) and 25 units of 5' deadenylase (NEB M0331) were added and the reactions were incubated for 15 minutes at 30° C., 15 minutes at 37° C. and 5 minutes at 75° C.

5 units of UDG (NEB M0280) and 20 units of Endonuclease IV (EndoIV) (M0304) were added and reactions were incubated for an additional hour at 37° C. Although in this case, UDG and Endo IV were added after lambda exonuclease and deaminase, the enzymes could have been added in any order, before, during or after.

The 5' ligation was then performed by adding ATP to a final concentration of 1 mM, 5 pmol of the 5' adapter (5 pmol top strand, 10 pmol bottom strand) and 20 units of T4 RNA ligase 2 (NEB M0239). The reaction was incubated at 37° C. for 1 hour. Reverse transcription was performed by adding 50 mM final concentration of Tris-HCl buffer (pH 7.5), 75 mM final concentration of potassium chloride, 10 mM final concentration of DTT, 500 µM final concentration of each DNTP, 20 units of Murine RNase inhibitor (NEB M0314), 200 units of ProtoScript II Reverse Transcriptase (NEB M0368) and nuclease free water to bring the final volume to 50 µL. This reaction was then incubated for 1 hour at 42° C. First strand cDNA products were purified using NEBNext sample purification beads (NEB E7767) and 100% Isopropanol. Reactions were washed and eluted in nuclease free water according to the manufacturer's directions. PCR amplification of the library was performed using NEBNext High-Fidelity 2×PCR Master Mix (NEB M0541) and 25 pmol each of the forward and reverse primers. PCR was performed with the following program: an initial denaturation of 98° C. for 30 seconds followed by a varying number of cycles depending on the input ratio of RNA to adapters of: 98° C. for 10 seconds, 62° C. for 30 seconds. This was followed by a final elongation step of 72° C. for 5 minutes. Libraries were size selected using the NEBNext sample purification beads (NEB E7767) and using the small RNA library size selection protocol from the NEBNext Small RNA Library Kit (NEB E7330). Purified libraries were assayed on the Agilent 2100 Bioanalyzer to assess purity and concentration before being pooled and sequenced using 50 cycles of single-end Illumina sequencing.

TABLE 1

Improvement in the average number of microRNAs detected using a randomized splint adapter described in FIG. 1 compared with a single stranded adapter

| Tissue | BioChain Lot number | Donor Age | Donor Sex | Technique Type of 3' adapter | Tissue type | Average number of miRNA detected (rpm >5) | Number differentially expressed (probability >0.9) | Shared Differential Expression |
|---|---|---|---|---|---|---|---|---|
| Stomach | A612105 | 51 | M | Single | Normal | 302.0 | 45 | 38 |
| | | | | stranded | Tumor | 333.0 | | |
| | | | | Randomized | Normal | 441.0 | 57 | |
| | | | | Splint | Tumor | 479.0 | | |
| Lung | B501175 | 67 | M | Single | Normal | 315.0 | 22 | 18 |
| | | | | stranded | Tumor | 328.0 | | |
| | | | | Randomized | Normal | 404.5 | 73 | |
| | | | | Splint | Tumor | 476.5 | | |
| Kidney | A610274 | 2 | M | Single | Normal | 349.0 | 72 | 53 |
| | | | | stranded | Tumor | 349.5 | | |
| | | | | Randomized | Normal | 504.0 | 86 | |
| | | | | Splint | Tumor | 496.0 | | |
| Breast | B610021 | 56 | F | Single | Normal | 330.5 | 29 | 15 |
| | | | | stranded | Tumor | 332.5 | | |
| | | | | Randomized | Normal | 447.5 | 29 | |
| | | | | Splint | Tumor | 464.0 | | |

What is claimed is:

1. A method comprising:

ligating 3' adaptor molecules to the ends of members of a population of single stranded target polynucleotides, wherein the 3' adaptor molecules comprise:

a top strand and a bottom strand, wherein:

(a) the top strand comprises a nucleic acid sequence that is complementary to a portion of the nucleic acid sequence of the bottom strand, such that the top strand and bottom strand form a double-stranded region by complementary base-pairing; and (b) the bottom strand comprises: (i) a non-complementary 3' single-stranded extension, (ii) a sequence of at least 4 degenerate nucleotides, wherein the at least 4 degenerate nucleotide sequence is a random sequence, wherein the random sequences the 3' adaptor molecules bind to members of the population of single stranded target polynucleotides; and (iii) a site-specific cleavable sequence or nucleotide at or near the junction between the double-stranded region and the single-strand extension, suitable f removing the single-strand extension by cleavage to form a double-stranded region at t 3' end of the target polynucleotides;

cleaving the single-strand extensions of the ligated 3' adaptors;

ligating 5' adaptors to the 5' ends of the single stranded target polynucleotides, wherein the 5' polynucleotide adaptors comprise a top strand and a complementary bottom strand with the bottom strand having a 5' single-strand extension containing degenerate bases.

2. The method according to claim 1, wherein the single stranded target polynucleotides are RNA.

3. The method according to claim 2, wherein the polynucleotides are members of a library.

4. The method according to claim 2, wherein the polynucleotides are members of a population of RNAs that are variable in size and concentration.

5. The method according to claim 4, further comprising, after ligating the 3' adaptor molecules, cleaving the single-strand extensions of the ligated 3' adaptors, and ligating 5' adaptors: reverse transcribing the RNA and forming a cDNA library.

6. The method according to claim 5, further comprising: performing the steps of ligating the 3' adaptor molecules, ligating the 5'adaptors and reverse transcribing the RNA in a one pot workflow.

7. The method according to claim 5, wherein a purification step is not performed prior to reverse transcribing the RNA and forming the cDNA library.

8. The method according to claim 2, wherein the RNA is sRNA.

9. The method according to claim 1, wherein the step of cleaving the single-strand extensions of the ligated 3' adaptors comprises cleaving a site-specific cleavable sequence or nucleotide in the 3' adaptors with a nicking restriction endonuclease.

10. The method according to claim 1, wherein the step of cleaving the single-strand extensions of the ligated 3' adaptors comprises cleaving a site-specific cleavable sequence or nucleotide in the 3' adaptors with a glycosylase/lyase.

11. The method according to claim 1, wherein the single stranded target polynucleotides are RNA in a body fluid.

12. The method according to claim 1, wherein the single stranded target polynucleotides are RNA in a cell lysate.

13. The method of claim 1, wherein cleaving the single-strand extensions of the ligated 3' adaptors is performed before ligating 5' adaptors.

14. The method of claim 1, wherein cleaving the single-strand extensions of the ligated 3' adaptors is performed after ligating 5' adaptors.

15. The method of claim 1, wherein the top strand and bottom strand of the 3' adaptor molecules are formed from two polynucleotide strands.

16. The method of claim 1, wherein the top strand and bottom strand of the 3' adaptor molecules are formed from a single polynucleotide strand.

* * * * *